United States Patent [19]

Py

[11] Patent Number: 4,946,452
[45] Date of Patent: Aug. 7, 1990

[54] OCULAR TREATMENT APPARATUS

[76] Inventor: Daniel Py, 54 Falmouth St., Short Hills, N.J. 07078

[21] Appl. No.: 267,526

[22] Filed: Nov. 4, 1988

Related U.S. Application Data

[63] Continuation-in-part of Ser. No. 118,388, Nov. 6, 1987, Pat. No. 4,792,334.

[51] Int. Cl.$^5$ ............................................. A61H 33/04
[52] U.S. Cl. ...................................... 604/301; 604/295
[58] Field of Search ........................... 604/214, 295–302

[56] References Cited

U.S. PATENT DOCUMENTS

| | | | |
|---|---|---|---|
| 3,279,446 | 10/1966 | Mings | 604/302 |
| 4,085,750 | 4/1978 | Bosshold | 128/233 |
| 4,131,115 | 12/1978 | Peng | 128/249 |
| 4,386,608 | 6/1983 | Ehrlich | 604/298 |
| 4,531,944 | 7/1985 | Bechtle | 604/302 |
| 4,543,096 | 9/1985 | Keene | 604/302 |
| 4,605,398 | 8/1986 | Herrick | 604/300 |
| 4,685,906 | 8/1987 | Murphy | 604/300 |
| 4,733,802 | 3/1988 | Sheldon | 604/302 X |
| 4,792,334 | 12/1988 | Py | 604/301 |

OTHER PUBLICATIONS

Sheldon, G. M., "Self-Administration of Eyedrops," *Opthalmic Surgery*, May 1987, pp. 393–394.
Letocha, Charles E., "Methods for Self-Administration of Eyedrops," *Ann Ophthalmol*, 17:768–769 (1985).

*Primary Examiner*—Allen M. Ostrager
*Attorney, Agent, or Firm*—Kenyon & Kenyon

[57] ABSTRACT

An ocular treatment apparatus for applying medicament into an eye has an inner housing member with an eyepiece on a free end thereof. The eyepiece defines an opening in one end thereof, and the opening has a peripheral edge shaped for engagement with the facial tissue surrounding an eye. A body portion of the inner housing member is coupled to the eyepiece and is dimensioned to receive a vial of medicament for application to the eye. An outer housing member of the apparatus has an open free end, which is slidably engaged over the inner housing member. The outer housing member has a displacement rod that projects inwardly from a closed end thereof in the axial direction of the apparatus. The displacement rod is engageable with a flexible vial supported within the body portion of the inner housing member. The displacement rod flexes the vial inwardly to dispense medicament therefrom into an eye. A flexible bar is mounted to the outer housing member, and the free end of the flexible bar is adapted to be engaged with the facial tissue below an eye to displace the facial tissue, and thus displace the lower eyelid, to direct the medicament into the exposed ocular cul-de-sac of the eye. The flexible member is engaged with the facial tissue by moving the outer housing member toward the eyepiece, which simultaneously displaces the lower eyelid and allows the medicament dispensed from the vial to fall into the exposed ocular cul-de-sac of the eye.

31 Claims, 5 Drawing Sheets

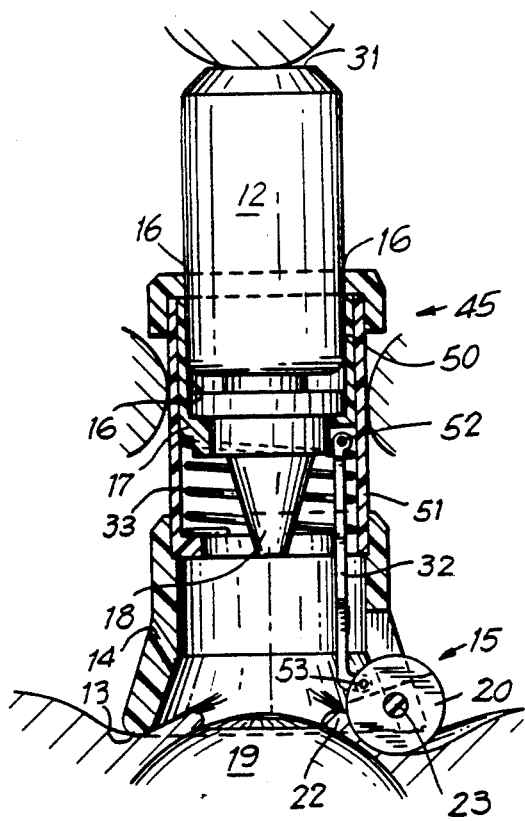
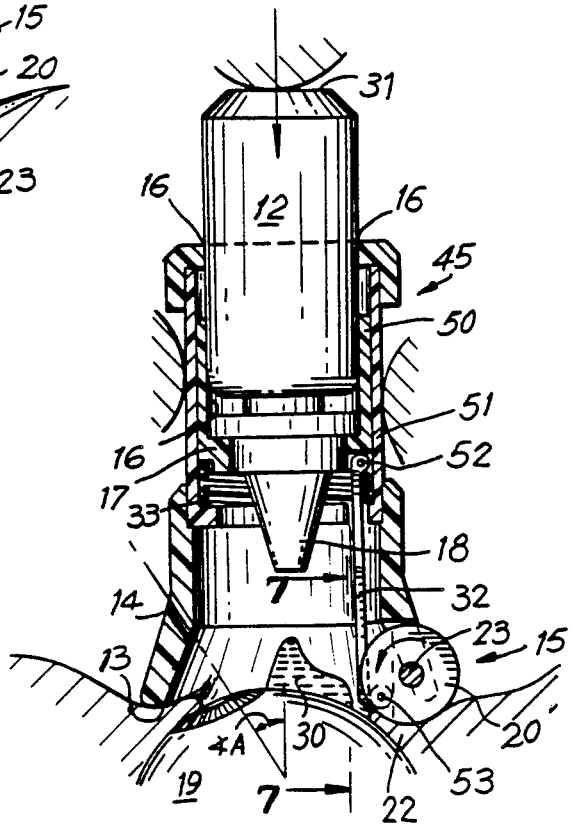
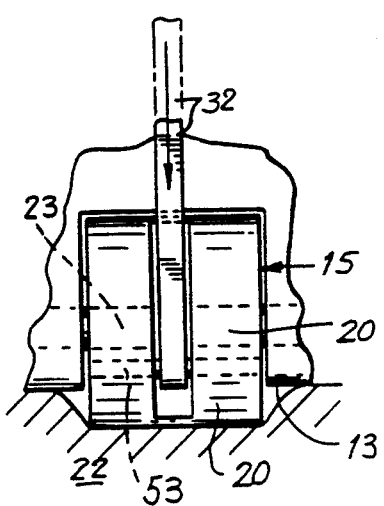
FIG. 5
FIG. 6
FIG. 7

OCULAR TREATMENT APPARATUS

This application is a continuation-in-part of U.S. application Ser. No. 07/118,388 filed Nov. 6, 1987 now U.S. Pat. No. 4,792,334.

BACKGROUND OF THE INVENTION

This invention is directed to an ocular treatment apparatus and, in particular, to an ocular treatment apparatus that can apply eye drops of liquid medicament safely and easily. Specifically, most people encounter difficulty in applying drops to their eyes. The eye is known to be a very sensitive body part and individuals find it difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Additionally, elderly people often have difficulty holding a dropper bottle steady or encounter difficulty in squeezing the bottle to apply a proper quantity of the medicament.

Even if the liquid medicament is properly applied to the cornea, the medicament's effectiveness is limited. The maximum volume of a drop of liquid medicament which can be introduced into contact with an eye at one time is about 30 microliters. Any amount that is greater usually spills over the eyelid onto the cheek. When eye drops are applied to the surface of the eyeball, blinking and natural tear flow combine to limit the time to a few minutes that liquid medicament will remain effective. However, if medicament is applied to the cul de sac of the conjunctiva, the medicament will remain effective for a longer period of time, maximizing the benefits of applying drops of liquid medicament to the eye.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for depressing the lever and simultaneously causing the eyelids to spread apart while forcing a drop from the dropper bottle. However, the apparatus described in U.S. Pat. No. 4,543,069 will not properly steady the eyeball nor expose the cul de sac. Further, the finger-like projections could cause injury to the eye if a user accidentally contacts his cornea with one of the projections. Similarly, U.S. Pat. No. 4,531,944 depicts an apparatus for steadying the tip of a dropper over the eye and further includes a sighting hole to distract the eye. However, this apparatus does not have a means to expose the cul de sac nor keep the lower eyelid depressed.

Accordingly, an ocular treatment apparatus that is capable of simultaneously steadying the eyeball, orienting the application of the medicament, applying the medicament and exposing the cul de sac is desired.

SUMMARY OF THE INVENTION

Generally speaking, in accordance with the invention, an ocular treatment apparatus is provided for applying liquid medicament from a reservoir. The apparatus includes a tubular housing with a first open end adapted to conform to the shape of the facial area surrounding the eye socket. The housing is constructed and arranged to receive, hold and position a reservoir containing the liquid medicament. A sighting opening is included on the housing to properly orient the eye and distract the user from the drops of liquid medicament to be introduced into the eye. An eyelid displacement mechanism is supported on the first open end of the housing at a position diametrically opposed to the sighting opening. The displacement mechanism is adapted to evert the lower eyelid and expose the cul de sac. This combination of an eye focused at the sighting hole and an everted lower eyelid exposes the cul de sac so that drops of medicament dispensed into the eye will more easily and directly be applied at or near the cul de sac where it is temporarily retained to increase the length of time the medicament will medicate the eyeball. In a further embodiment of the instant invention, the lower eyelid displacement mechanism will simultaneously cause drops to be emitted from the reservoir into the cul de sac as the lower eyelid is everted to facilitate application of the drops of liquid medicament The cul de sac is a low sensitivity area as opposed to the cornea area therefore application of medicament to the cul de sac is more comfortable In another embodiment of the invention an ocular treatment apparatus for applying solid or liquid medicament into an eye comprises an inner housing member including an eyepiece portion on a free end thereof. The eyepiece portion defines an opening therein having a peripheral edge shaped for conformable engagement with the facial tissue surrounding an eye. The inner housing member further includes a body portion for receiving a vial of liquid medicament for application to the eye.

An outer housing member of the apparatus has an open free end slidably engaged over the end of the inner housing member opposite the eyepiece portion. The outer housing member defines a medicament displacement member projecting outwardly from its end opposite the free end and projecting into the body portion of the inner housing member. The displacement member is depressible against a flexible vial contained within the body portion of the inner housing member by sliding the outer housing member toward the eyepiece portion for displacing medicament from the vial and, in turn, through the opening in the eyepiece portion and into the eye.

The apparatus further includes means for displacing the lower eyelid of an eye to evert the lower eyelid so that medicament released from the vial is applied to the ocular cul de sac of the eye. The means for displacing the lower eyelid preferably include a cushion member having a substantially curved configuration The cushion member is disposed around the peripheral edge of the eyepiece portion so that the free end of the cushion member is placed between the interior surface of the eyepiece portion and facial tissue of the person. The other end of the cushion member is connected to a flexible bar which, in turn, is connected on its other end to the outer housing member. The flexible bar member presses the cushion member downwardly to evert the lower eyelid when the outer housing member is moved over the inner housing member toward the eyepiece portion for application of medicament into the ocular cul de sac.

Accordingly, it is an object of this invention to provide an improved ocular treatment apparatus for facilitating the application of drops of liquid medicament to the eye.

Another object of the invention is to provide an improved ocular treatment apparatus capable of simultaneously displacing the lower eyelid and steadying and orienting the eyeball so that liquid medicament may be safely and easily applied.

A further object of the invention is to provide an improved ocular treatment apparatus wherein the ocular cul de sac is exposed during application of drops of liquid medicament.

Still another object of the invention is to provide an ocular treatment apparatus which facilitates the orienting of a medicament reservoir over the eye, displaces the lower eyelid, and emits the liquid medicament from the reservoir.

Still other objects and advantages of the invention will in part be obvious and will in part be apparent from the specification and drawings The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 5 is a sectional view of an alternative embodiment of the ocular treatment apparatus;

FIG. 6 is a sectional view illustrating the operation of the apparatus shown in FIG. 5; and FIG. 7 is a sectional view taken along line 7—7 of FIG. 6.

DETAILED DESCRIPTION OF THE PREFERRED EMBODIMENTS

Figure 1:
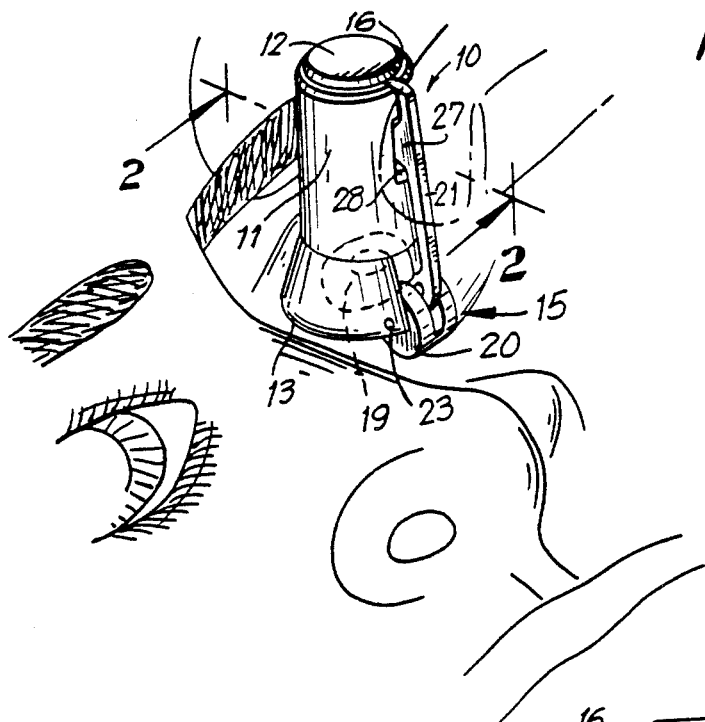
FIG. 1 is a perspective view of a preferred embodiment of the ocular treatment apparatus.
Figure 2:
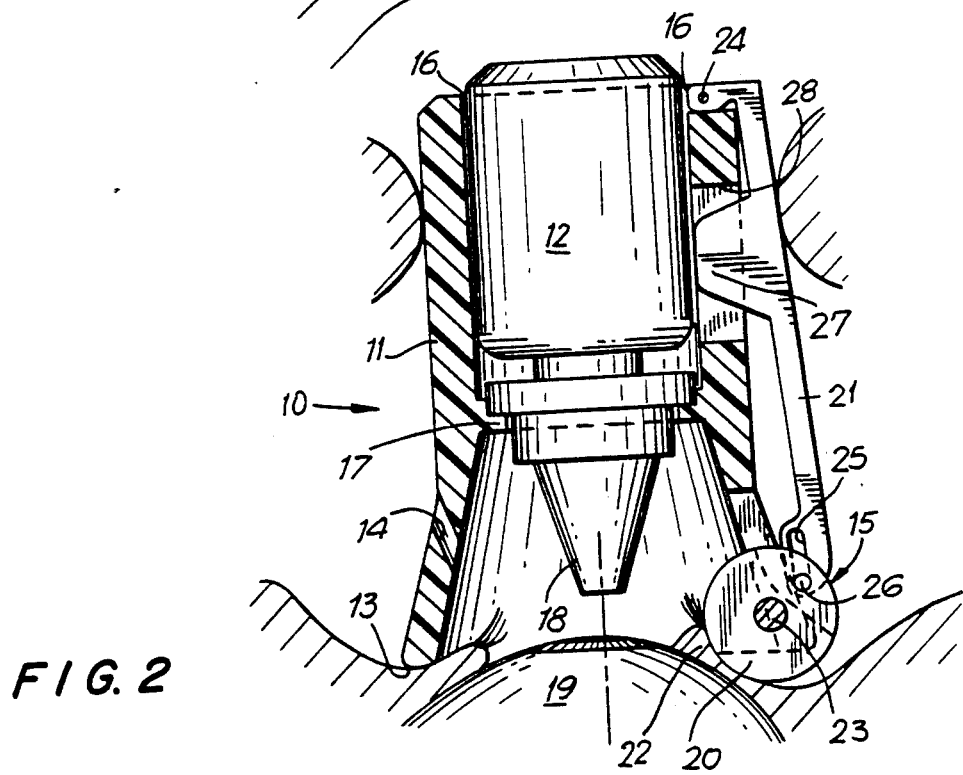
FIG. 2 is a sectional view taken along line 2—2 of FIG. 1.
Figure 3:
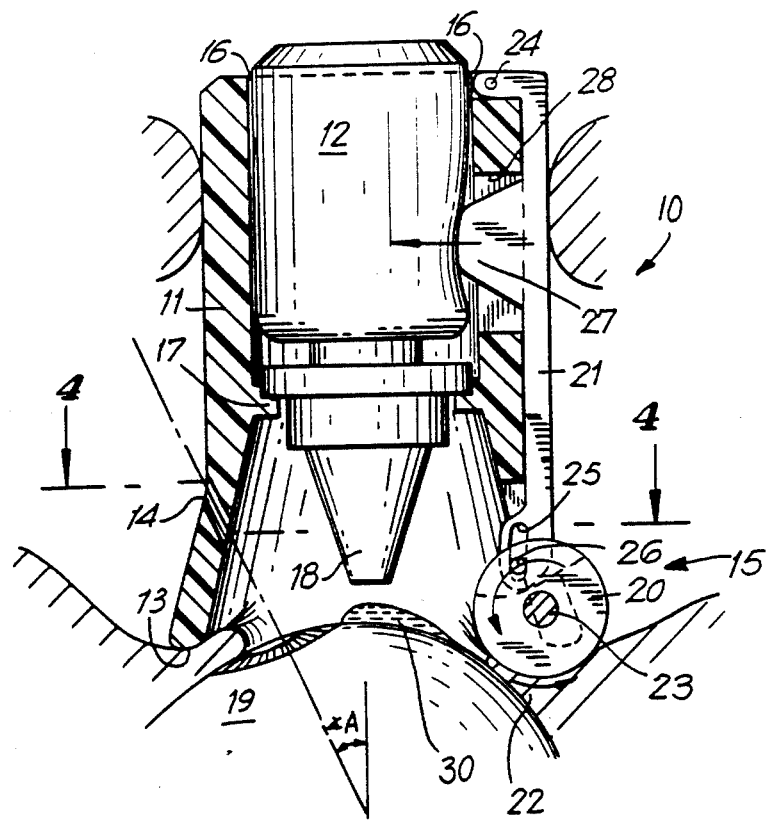
FIG. 3 is a sectional view taken along line 2—2 of FIG. 1 illustrating the operation of the ocular treatment apparatus.
Figure 4:
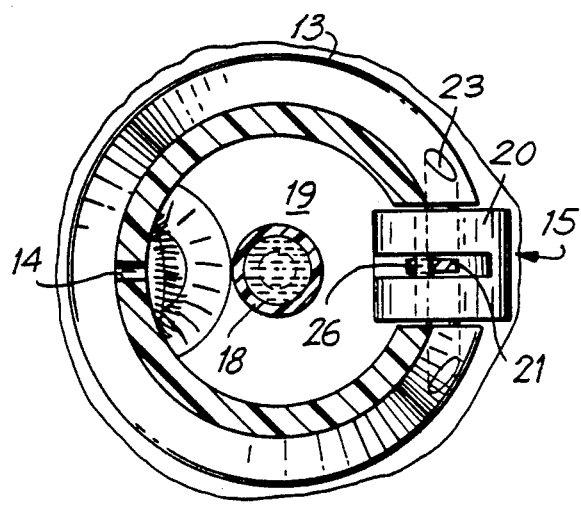
FIG. 4 is a sectional view taken along line 4—4 of FIG. 3.

Referring generally to FIGS. 1 to 4, a preferred embodiment of the ocular treatment apparatus of the instant invention is indicated generally at 10. Apparatus 10 includes a tubular housing 11 constructed and arranged to receive and hold a dropper bottle 12. Housing 11 includes a front opening 13 which conforms to the facial area surrounding an eye 19. A sighting opening 14 is positioned in the tubular housing proximate to front opening 13 to properly orient an eyeball during use of the ocular treatment apparatus. A displacement mechanism, illustrated generally at 15, is included on housing 11 at a position generally diametrically opposite sighting opening 14. Displacement mechanism 15 retracts the lower eyelid to expose a surface of the eye below the pupil for application of medicament from reservoir 12.

In an exemplary embodiment, housing 11 is constructed and arranged to retain a dropper bottle 12. However, the housing can be modified to hold a dropper, single dose dropper vial, pressurized propellant device or any other suitable applicator that stores and can deliver liquid medicament to the eye.

Accordingly, housing 11 includes a rear opening 16 shaped to receive dropper bottle 12. Housing 11 includes a radially disposed collar 17 for receiving and releasably securing the neck of dropper bottle 12. Housing 11 is configured so that the longitudinal axis of dropper bottle 12 is substantially parallel to and substantially aligned with the longitudinal axis of housing 11.

Front opening 13 is configured to nest in the facial area surrounding the eye socket. It is shaped so that apparatus 10 may be placed over the eye and easily maintained in a steady position with the tip of a dropper bottle nozzle 18 correctly positioned over eye 19. In this manner, when front opening 13 is positioned to surround the eye and a person tilts his head back the drop of medicament falling from nozzle 18 will fall into the eye 19 by gravity.

An eyelid displacement mechanism, located generally at 15, for safely and comfortably retracting the lower eyelid is included in the ocular treatment apparatus. It is desirable for the medicament to flow to the interior cul de sac to increase the effectiveness of the medicament. Sliding the lower eyelid back and down helps to uncover the ocular cul de sac which is a nonsensitive part of the conjunctiva. Displacement mechanism 15 includes an engagement body 20 and drive member 21. Engagement body 20 is a curved member which contacts lower eyelid 22 when front opening 13 is positioned around the eye. Engagement body 20 is rotatably mounted to housing 11 at front opening 13 by axle 23. When curved engagement body 20 is caused to partially rotate, it everts lower eyelid 22 and exposes the cul de sac.

The curved design of engagement body 20 provides several important benefits. The area of contact between the curved surface of engagement body 20 and lower eyelid 22 is considerable. This helps evert the eyelid properly and feels similar to using one's own finger to evert the eyelid. The wide engagement surface also makes exact placement of the engagement body 20 less critical. The curved surface of engagement body 20 also prevents injuries which can occur when an instrument for sliding the eyelids back is utilized.

To utilize apparatus 10, front opening end 13 is placed over the eye with engagement body 20 resting against lower eyelid 22. As depicted generally in FIG. 3, an elongated drive shaft 21 is then displaced to partially rotate engagement body 20. A first end of drive shaft 21 is pivotally connected to housing 11 by pivot pin 24. A second end of drive shaft 21 is pivotally and slideably connected to engagement body 20 at slot 25, which is positioned around drive pin 26. Drive shaft 21 includes a projection 27 intermediate its first and second ends. Housing 11 defines a housing slot 28 through rear opening 16 aligned with projection 27 so that when drive shaft 21 is moved towards housing 11, projection 27 will pass through housing slot 28 to compress dropper bottle 12 and force drops 30 of liquid medicament from nozzle 18. As drive shaft 21 moves towards housing 11, the sides of slot 25 push against drive pin 26 to partially rotate engagement body 20 to retract lower eyelid 22 coincident with liquid 30 being introduced to the eye from nozzle 18.

Sighting opening 14 is positioned proximate front open end 13 to correctly orient the eye and help uncover the cul de sac. It also helps control reflexive blinking which is often caused by the user sensing something approaching his exposed eye. Sighting opening 14 is provided in housing 11 near front opening 13 at a position diametrically opposed to curved engagement body 20 so that a user will have his eye steadied in an upwardly rotated position when his lower eyelid is everted. To properly uncover the cul de sac, sighting opening 14 should be positioned near front opening 13 so that the eye will be oriented upwardly though an angle A which should be at least 30°. However, in a preferred embodiment angle A is greater than 35°. Because the only light perceived by the user passes through sighting hole 14, a person having poor vision is assisted in properly orienting their eyeball Referring next to FIGS. 5 through 7, a further embodiment of the ocular treatment apparatus, generally indicated as 45 is depicted, like reference numerals being utilized to depict like elements discussed above. This embodiment has the same curved engagement body 20, front opening 13, sighting hole 14 and collar 17. However, the mechanism for rotating engagement body 20 is structurally distinct. Bottle 12 rests in slidable seat 50. Seat 50 can slide within outside tubular housing 51 and is upwardly biased by spring 33. Vertical drive shaft 32 has two ends. Its first end is pivotably connected to slideable seat 50 by pin 52. The second end of vertical drive member 32 is slideably and pivotally connected to curved engagement body 20, by drive pin 53. When bottle 12 is inserted into the housing to compress spring 33, vertical drive shaft 32 causes curved engagement body 20 to partially rotate, everting lower eyelid 22.

Specifically, a user places front opening 13 of apparatus 45 over the eye and contacts the lower eyelid with engagement body 20. To dispense drops of liquid medicament, the user again peers through sighting opening 14. To evert the lower eyelid, end 31 of dropper bottle 12 is pushed into the housing, causing vertical drive member 32 to rotate curved engagement body 20.

Accordingly, this further embodiment causes the force necessary to evert the lower eyelid to be applied in a direction which will increase the contacting pressure between engagement body 20 and lower eyelid 22. This will decrease the chance of slippage to insure that lower eyelid 22 is everted. Spring 33 returns the apparatus to its original position shown in FIG. 5.

Accordingly, when the ocular treatment apparatus of the instant invention is used to apply liquid medicament to the eye, the above indicated advantages are observed. The dropper bottle is steadied over the eye in a correct orientation; the cul de sac of the conjunctiva is exposed by the combination of orienting the eyeball in an upwardly gazing position while everting the lower eyelid; involuntary blinking is prevented by the user focusing on light passing through the sighting opening at the same time that the lower eyelid is held in a depressed position. Therefore, drops of liquid medicament can be applied to the eye so that the medicament will flow to the cul de sac to increase the half life of its effectiveness.

Turning to FIGS. 8 through 11 another embodiment of the ocular treatment apparatus of the invention is illustrated generally as 110. The apparatus 110 includes an inner housing 112 slideably engaged within an outer housing 114. The inner housing 112 includes an eyepiece portion 120 and a substantially cylindrical portion 116 having an open end 118. The peripheral edge of the eyepiece portion 120 defines an open end 122 shaped to conform to the contour of the facial tissue surrounding the eye. The eyepiece portion 120 has defined in an upper wall thereof a sighting opening 124. The sighting opening 124 is located near the open end 122 of the eyepiece and operates to help correctly orient the eye for uncovering the cul de sac in the same manner as the sighting opening 14 described above in relation to the previous embodiments Sighting opening 124, therefore, is similarly positioned so that the eye will be oriented upwardly through an angle A which is at least 30°. When the eyepiece 120 is placed against the facial tissue around the eye the shape of the peripheral edge of the eyepiece prevents light from passing between the eyepiece and facial tissue, so that substantially all of the light entering the eye enters through the sighting opening 124.

The inner housing 112 of apparatus 110 defines an elongated channel 128 in an outer wall thereof extending in the axial direction of the apparatus. The end of channel 128 near the open end 118 of inner housing 112 is shaped to form a seat 130 recessed in the channel 128 for a ball 132. The ball 132 is preferably made of metal, such as steel. When the apparatus 110 is rotated and aligned over the eye, the ball 132 rolls from the recessed seat 130 and into the channel 128. In this manner, the ball 132 rolls down the channel 128 and hits the bottom wall thereof. The action of the ball striking the bottom wall of the channel transmits vibrations through the wall of the apparatus 110 and into the facial tissue and bone structure of the person. In this way the person can feel or hear the falling ball and thus know when the apparatus is properly aligned over the eye. This is especially useful for persons that have poor eyesight or are deaf, since they can simply feel the vibrations of the rolling ball.

The apparatus 110 further includes a substantially cylindrical shaped vial 134 for containing liquid medicament. The vial 134 is shaped to slidably fit within the cylindrical portion 116 of inner housing 112. The vial includes a body 136 for holding liquid medicament, a neck 138, and a nozzle 140 for releasing drops of liquid. The body 136 of the vial is attached to the inner housing 116 in a known manner, such as, for example, by forming a snap fit. Similarly, the body 116 may be molded as a single piece with the inner housing 116. The shape of the nozzle 140 is known, and may be the same as the nozzle 18 described above in relation to the previous embodiments. The body 136 of the vial defines a cavity 142 therein coaxial with the apparatus 110 and extending along a substantial portion of the body 136. As can be seen, the closed end of cavity 142 is located near the opening of neck 138. The vial 138 is formed of a flexible plastic material, and, as will be hereinafter described, the closed end of cavity 142 is pressed forward in order to release medicament into the eye.

The outer housing 114 of apparatus 110 is slideably engaged over inner housing 112 through an open end 144. Outer housing 114 further defines a closed end 146 and a displacement member 148 projecting outwardly from closed end 146 and coaxial with the apparatus 110. A first lobe 150 is formed in the outer wall of inner housing 112, and second lobe 152 is formed on the inner wall of outer housing 114 below first lobe 152 to prevent outer housing 114 and inner housing 112 from sliding apart. As can be seen, by pressing outer housing 114 toward eyepiece 120 the displacement member 148 forces the closed end of cavity 142 forward in order to displace medicament into the eye. Third lobes 154, 154 are preferably formed on the outer wall of the inner housing 112 below first lobe 150 and second lobe 152 in order to limit the downward stroke of outer housing 114, and thus, permit only a predetermined volume of medicament to be displaced through nozzle 140.

Figure 8:
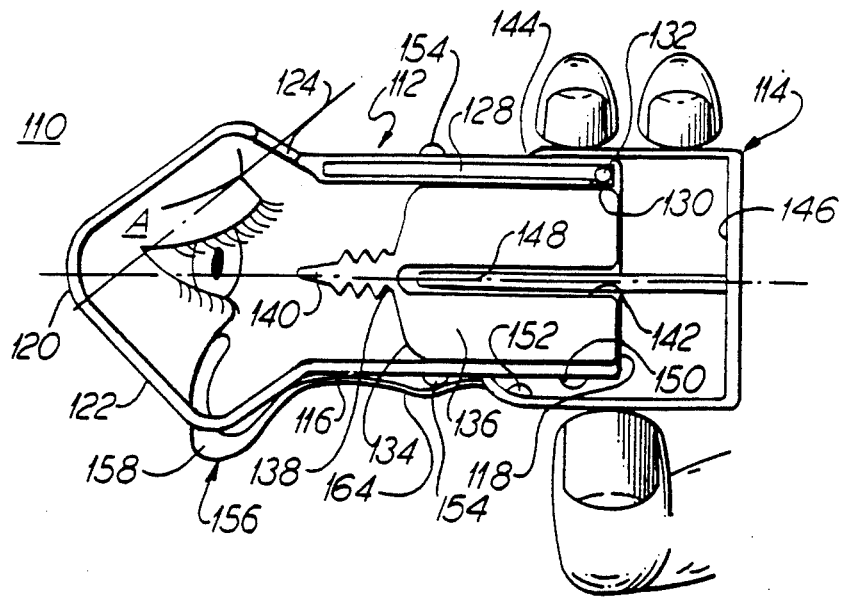
FIG. 8 is a side planar view in partial cross section of another ocular treatment apparatus embodying the invention shown placed over an eye.
Figure 9:
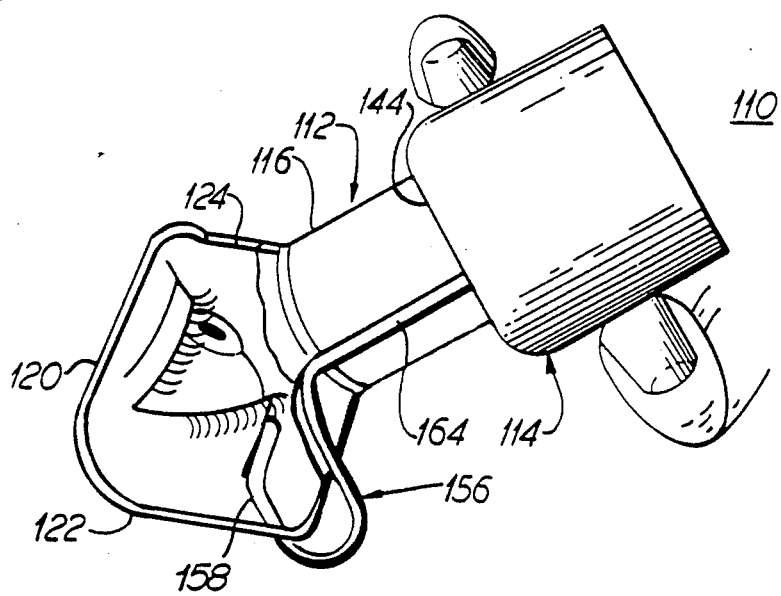
FIG. 9 is a side planar view of the apparatus of FIG. 8 shown aligned over an eye and illustrating a partial cross sectional view of the eyepiece portion.
Figure 10:
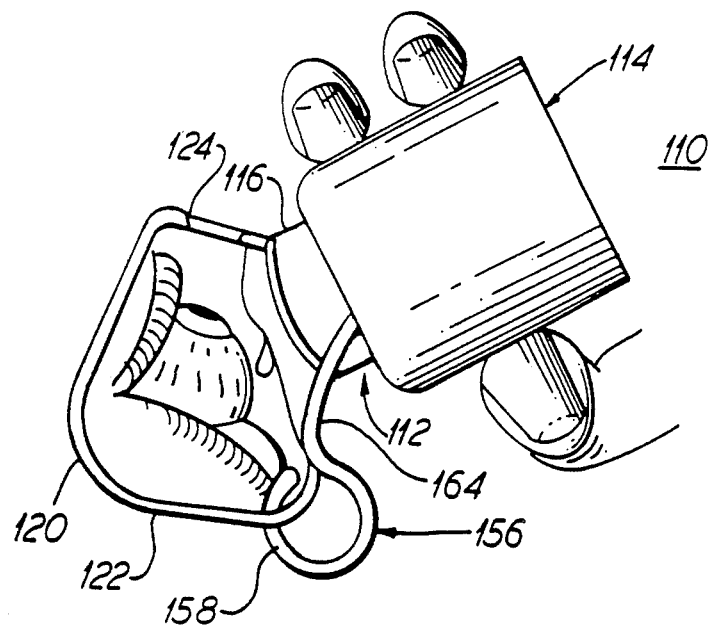
FIG. 10 is a side planar view of the apparatus of FIG. 8 shown applying a drop of liquid medicament into an eye and also illustrating a partial cross sectional view of the eyepiece portion.
Figure 11:
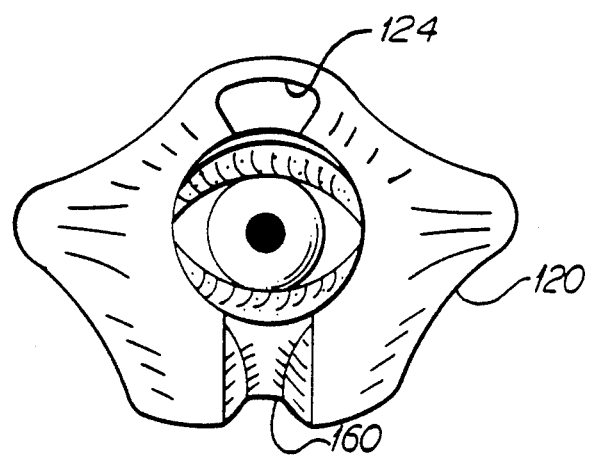
FIG. 11 is a front planar view illustrating the eyepiece portion of the apparatus of FIG. 8.

The apparatus 110 further includes a cushion member 156 formed of a flexible polymeric material. The cushion member 156 includes on its free end a pad 158 having a generally curved shape to fit around the edge of eyepiece 120 and rest between the inner surface of eyepiece 120 and the facial tissue of the person, as best shown in FIGS. 8 through 10. Turning to FIG. 11, eyepiece 120 further defines an indentation 160 formed in a surface thereof and extending radially through the peripheral edge in an area diametrically opposed to sighting opening 124. As can be seen, the free end of pad 158 is slidably fitted around the edge of eyepiece 120 and through indentation 160. The other end of pad 158 is connected to one end of a flexible plastic bar 164 of the cushion member which, in turn, is connected on its other end to the edge of open end 144 of outer housing 114. The bar 164 of the cushion member is attached to outer housing 114 in a known manner, such as, for example, by ultrasonic welding.

The cushion member 156 is provided for safely and comfortably retracting downwardly the lower eyelid in order to permit medicament to flow to the interior cul de sac, and thus, increase the comfort to the person and effectiveness of treatment. The free end of pad 158 contacts the lower eyelid 22 when eyepiece 120 is positioned over the eye. When the outer housing 114 is pressed toward the eyepiece 120, the flexible bar 160, in turn, presses pad 158 against the indentation 160, and thus, gently presses the pad downwardly to evert the lower eyelid 22 and expose the cul de sac, as illustrated in FIGS. 9 and 10. When the pressure is released from the outer housing the flexible bar 164 pushes outer housing 114 back toward its initial position and away from inner housing 112.

To utilize apparatus 110, eyepiece 120 is placed over the eye so that it is conformably engaged with the facial tissue surrounding the eye, as shown in FIG. 8. The user then looks through sighting opening 124 to properly orient the eye and tilts his or her head back so that the apparatus 110 is rotated toward a vertical position, as shown in FIG. 9. The user knows that the apparatus has been rotated far enough when the ball 132 is displaced from its seat 130 and hits the bottom wall of channel 128. The user then presses the outer housing toward the eyepiece.

The displacement member 148, in turn, simultaneously forces the closed end of cavity 142 toward nozzle 140 and displaces a predetermined volume of medicament through nozzle 140 and into the eye, as shown in FIG. 10. The downward stroke of outer housing 114 simultaneously causes the plastic bar 162 to press pad 158 against the indentation 160, and thus, gently press the pad downwardly to evert the lower eyelid 22 and expose the cul de sac to receive the liquid or solid medicament.

It will thus be seen that the objects set forth above, among those made apparent from the preceding description, are efficiently attained and, that certain changes may be made in the above constructions without departing from the spirit and scope of the invention. For example, the medicament vial 134 of apparatus 110 may be an aerosol container that releases medicament under pressure and without the need for displacement member 148. Therefore, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An ocular treatment apparatus for applying medicament into an eye, said apparatus comprising:

an inner housing member including an eyepiece portion on a free end thereof, said eyepiece portion having a peripheral edge defining an opening, said peripheral edge being shaped for conformable engagement with the facial tissue surrounding an eye, said inner housing member further including a body portion connected to said eyepiece portion for receiving a vial of medicament for application to the eye;

an outer housing member defining an open free end, said open end being slideably engaged over the other end of said inner housing member, said outer housing member further defining a medicament displacement member projecting outwardly from the end opposite said free end and into said body portion of said inner housing member, said displacement member being depressible against a flexible vial received within said body portion of said inner housing member by sliding said outer housing member toward said eyepiece portion to displace medicament from the vial and, in turn, through said opening in said eyepiece portion and into the eye; and means for displacing the lower eyelid of an eye coupled to said outer housing member, so that medicament released from the vial may be applied to the ocular cul-de-sac of the eye.

2. An ocular treatment apparatus as defined in claim 1, wherein said inner housing member defines an elongated channel in a wall thereof extending in the axial direction of said apparatus, said apparatus further includes a ball disposed in said channel, said ball sliding through said channel toward said eyepiece portion and striking the bottom wall of said channel when said apparatus is properly aligned over the eye for transmitting vibrations through said apparatus to the facial tissue and bone structure of the person for signalling that said apparatus is aligned.

3. An ocular treatment apparatus as defined in claim 2, wherein said means for displacing the lower eyelid of an eye includes a cushion member having a substantially curved configuration, said cushion member being disposed around the peripheral edge of said eyepiece portion so that the free end of said cushion member is placed between the interior surface of said eyepiece portion and the facial tissue of the person, the other end of said cushion member being connected to one end of a flexible bar member which, in turn, is connected on its other end to said outer housing member, said flexible bar member pressing said cushion member downwardly to displace the lower eyelid when said outer housing member is moved over said inner housing member toward said eyepiece portion.

4. An ocular treatment apparatus for applying medicament into an eye, said apparatus comprising:
   an inner housing member including an eyepiece portion on a free end thereof, said eyepiece portion having a peripheral edge defining an opening therethrough, said peripheral edge being shaped for conformable engagement with the facial tissue surrounding an eye, said inner housing member further including a body portion connected on one end to said eyepiece portion for receiving a container of medicament for application to the eye;
   an outer housing member having an open free end, said open end being slideably engaged over the other end of said body portion of said inner housing member;
   means coupled to said outer housing member for dispensing medicament from the container received within said body portion through said eyepiece portion and into the eye; and
   means coupled to said outer housing member for displacing the lower eyelid of an eye to expose the ocular cul-de-sac, so that medicament released from the container is applied to the exposed ocular cul-de-sac of the eye.

5. An ocular treatment apparatus as defined in claim 4, said apparatus further comprising:
   means for diverting the visual axis of an eye upwardly to facilitate application of medicament to the exposed ocular cul-de-sac of the eye.

6. An ocular treatment apparatus as defined in claim 5, wherein
   said means for diverting includes a sighting aperture extending through said eyepiece portion, wherein a user may look through said sighting aperture to divert the visual axis of the eye.

7. An ocular treatment apparatus as defined in claim 6, wherein
   said sighting aperture is located within said eyepiece portion so that a user's eye is diverted upwardly through an angle of about 30° when looking through said sighting aperture.

8. An ocular treatment apparatus as defined in claim 4, said apparatus further comprising:
   means for indicating to a user when said apparatus is properly aligned over the eye, said means for indicating being coupled to said inner housing member.

9. An ocular treatment apparatus as defined in claim 8, wherein
   said means for indicating includes a channel defined within a wall of said inner housing member, and a ball slidably disposed within said channel, said ball moving through said channel and hitting the bottom wall thereof when said apparatus is properly aligned over the eye, to transmit vibrations to the user to indicate that said apparatus is properly aligned.

10. An ocular treatment apparatus as defined in claim 4, wherein
    said outer housing member includes a substantially cylindrical shaped wall, said cylindrical shaped wall defining said open free end; and
    said inner housing member defines a substantially cylindrical shaped wall dimensioned to be slidably received within said cylindrical shaped wall of said outer housing member, such that said inner housing member may be slidably engaged within said outer housing member.

11. An ocular treatment apparatus is defined in claim 10, wherein
    said outer housing member further defines a closed end on one end of said substantially cylindrical shaped wall opposite said open free end; and
    said means for dispensing includes a rod member mounted to said closed end of said outer housing member and projecting inwardly toward said open free end thereof, the free end of said rod member being engageable with a container received within said body portion of said inner housing member to displace medicament from the container.

12. An ocular treatment apparatus as defined in claim 4, wherein
    said means for displacing includes a flexible member coupled on one end to said outer housing member, the free end of said flexible member being engageable with the facial tissue below the eye, to displace the lower eyelid when said outer housing member is moved toward said inner housing member.

13. An ocular treatment apparatus as defined in claim 12, wherein
    said flexible member includes a flexible bar coupled on one end to said outer housing member, and a flexible pad coupled to the other end of said flexible bar, the free end of said flexible pad being adapted for engagement with the facial tissue below an eye.

14. An ocular treatment apparatus as defined in claim 4, said apparatus further comprising:
    a medicament container, said medicament container including a vial portion for holding medicament, said vial portion being supported within said body portion of said inner housing member, said medicament container further including a nozzle portion coupled to said vial portion and in fluid communication therewith, to release medicament into an eye.

15. An ocular treatment apparatus as defined in claim 14, wherein
    said vial portion defines a flexible wall therein, said flexible wall being flexed inwardly by said means for dispensing, to dispense medicament within said vial portion through said nozzle portion and into an eye.

16. An ocular treatment apparatus as defined in claim 15, wherein
    said means for dispensing includes a rod member supported by said outer housing member, said rod member being engageable with said flexible wall by moving said outer housing member toward said inner housing member to dispense medicament from said vial.

17. An ocular treatment apparatus for applying medicament into an eye, said apparatus comprising:
    a first housing member, said first housing member including an eyepiece portion on one end thereof, said eyepiece portion defining an opening therethrough, the peripheral edge of said opening being shaped for engagement with the facial tissue surrounding an eye, said first housing member further including a body portion coupled to said eyepiece portion, said body portion being adapted to receive medicament to dispense the medicament into an eye;

a second housing member coupled to said first housing member and movable relative thereto;

means for dispensing medicament from said body portion of said first housing member through said eyepiece portion, said means for dispensing being coupled to said second housing member; and means for displacing the lower eyelid of an eye to expose the ocular cul-de-sac, and thus facilitate dispensing medicament onto the ocular cul-de-sac of the eye, said means for displacing being coupled to said second housing member.

18. An ocular treatment apparatus as defined in claim 17, said apparatus further comprising:

means for diverting the visual axis of a user's eye to further facilitate dispensing medicament to the exposed ocular cul-de-sac of the eye.

19. An ocular treatment apparatus as defined in claim 18, wherein said means for diverting includes a sighting aperture extending through said eyepiece portion, said sighting aperture being located so that a user may look through said sighting aperture to divert the visual axis of the eye.

20. An ocular treatment apparatus as defined in claim 17, wherein said second housing member is slidably engaged with said first housing member.

21. An ocular treatment apparatus as defined in claim 20, wherein said body portion is dimensioned to receive a vial of medicament.

22. An ocular treatment apparatus as defined in claim 21, wherein said means for dispensing includes a rod member supported by said second housing member and dimensioned to be engageable with a vial received within said first housing member, said rod member being engageable with the vial by moving said second housing member toward said first housing member to dispense medicament therefrom.

23. An ocular treatment apparatus as defined in claim 22, wherein said body portion of said first housing member defines a first substantially cylindrical shaped wall dimensioned to receive therein a vial of medicament; and said second housing member defines a second substantially cylindrical shaped wall defining an opening in one end thereof, said opening being dimensioned to slidably receive said first cylindrical shaped wall.

24. An ocular treatment apparatus as defined in claim 23, wherein said second housing member defines a closed end opposite said opening in one end thereof, said rod member being supported on one end by said closed end of said second housing member, the free end of said rod member being engageable with a vial of medicament received within said first housing member by sliding said second housing member toward said first housing member, to dispense medicament from the vial.

25. An ocular treatment apparatus as defined in claim 20, wherein said means for displacing includes a flexible member coupled to said second housing member, the free end of said flexible member being adapted to engage the facial tissue below the lower eyelid of an eye to move the facial tissue and displace the lower eyelid, by sliding said second housing member relative to said first housing member.

26. An ocular treatment apparatus as defined in claim 25, wherein said flexible member includes a flexible bar coupled on one end to said second housing member and a flexible pad coupled to the other end of said flexible bar, said flexible pad defining a substantially curved portion, the free end of said curved portion being fitted over the peripheral edge of said eyepiece portion and engageable with the facial tissue below an eye.

27. An ocular treatment apparatus as defined in claim 17, wherein said body portion defines a cavity therein adapted to receive medicament; and said apparatus further includes a nozzle portion supported by said body portion and in fluid communication with said cavity, said nozzle portion releasing medicament from said cavity through said eyepiece portion and into an eye.

28. An ocular treatment apparatus as defined in claim 17, wherein said body portion is dimensioned to receive a vial, wherein the vial includes a solid medicament.

29. An ocular treatment apparatus as defined in claim 17, wherein said body portion is adapted to receive an aerosol vial of medicament, wherein the vial releases the medicament under pressure.

30. An ocular treatment apparatus as defined in claim 17, said apparatus further comprising:

a vial of medicament, said vial being supported within said body portion.

31. An ocular treatment apparatus as defined in claim 30, wherein said vial defines a flexible wall, said flexible wall being engageable with said means for dispensing to dispense medicament therefrom.

* * * * *